United States Patent
Barbato et al.

(10) Patent No.: US 11,790,487 B2
(45) Date of Patent: Oct. 17, 2023

(54) IMAGE PROCESSING SYSTEMS AND METHODS OF USING THE SAME

(71) Applicant: Boston Scientific Scimed Inc., Maple Grove, MN (US)

(72) Inventors: Louis J. Barbato, Franklin, MA (US); George Wilfred Duval, Sudbury, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 197 days.

(21) Appl. No.: 17/221,621

(22) Filed: Apr. 2, 2021

(65) Prior Publication Data
US 2021/0312597 A1  Oct. 7, 2021

Related U.S. Application Data

(60) Provisional application No. 63/005,832, filed on Apr. 6, 2020.

(51) Int. Cl.
*G06T 3/40* (2006.01)
*G06T 7/13* (2017.01)
(Continued)

(52) U.S. Cl.
CPC ...... *G06T 3/4015* (2013.01); *A61B 1/000095* (2022.02); *A61B 1/00186* (2013.01);
(Continued)

(58) Field of Classification Search
CPC ....... G06T 3/4015; G06T 5/003; G06T 5/009; G06T 5/20; G06T 7/13; G06T 2200/32;
(Continued)

(56) References Cited

U.S. PATENT DOCUMENTS 7,030,917 B2 * 4/2006 Taubman ........... H04N 9/04515
358/518
7,474,337 B1    1/2009 Cooper
(Continued)

OTHER PUBLICATIONS

Xia, Wenyao, Elvis CS Chen, and Terry Peters. "Endoscopic image enhancement with noise suppression." Healthcare technology letters 5.5 (2018): 154-157. (Year: 2018).*

(Continued)

*Primary Examiner* — Andrae S Allison
(74) *Attorney, Agent, or Firm* — Bookoff McAndrews, PLLC (57) ABSTRACT

A medical device that includes a sensor including a filter array. The sensor is configured to capture a raw image and the filter array is configured to filter the raw image into a frame of raw pixel values including first, second, and third pixel values. The medical device includes non-transitory computer readable medium storing demosaicing instructions that, when executed, causes a processor to exclude the first pixel values from the frame of raw pixel values. The processor generates estimated second pixel values at locations of the excluded first pixel values and the third pixel values on the frame, and generates estimated third pixel values at locations of the excluded first pixel values and the second pixel values on the frame. The processor creates a processed image having a partial-resolution frame from the second pixel values, estimated second pixel values, third pixel values, and estimated third pixel values.

20 Claims, 4 Drawing Sheets

(51) Int. Cl.
*A61B 1/00* (2006.01)
*G06T 5/00* (2006.01)
*G06T 5/20* (2006.01)

(52) U.S. Cl.
CPC .............. *G06T 5/003* (2013.01); *G06T 5/009* (2013.01); *G06T 5/20* (2013.01); *G06T 7/13* (2017.01)

(58) Field of Classification Search
CPC . G06T 2207/10024; G06T 2207/10068; G06T 2207/20192; A61B 1/000095; A61B 1/00186; H04N 9/04557; H04N 9/04515
See application file for complete search history.

(56) References Cited

U.S. PATENT DOCUMENTS

| | | | |
|---|---|---|---|
| 10,210,599 B2* | 2/2019 | Zhao | H04N 9/04515 |
| 2005/0197536 A1* | 9/2005 | Banik | A61B 1/12 |
| | | | 600/179 |
| 2010/0177961 A1 | 7/2010 | Kalman | |
| 2010/0182466 A1 | 7/2010 | Chang et al. | |
| 2011/0063427 A1* | 3/2011 | Fengler | A61B 1/0005 |
| | | | 348/E5.09 |
| 2013/0075607 A1* | 3/2013 | Bikumandla | H01L 27/14634 |
| | | | 257/E31.127 |
| 2013/0300836 A1 | 11/2013 | Zhao et al. | |
| 2014/0307963 A1 | 10/2014 | Zimmer | |
| 2017/0178292 A1 | 6/2017 | Jiang et al. | |
| 2018/0153386 A1* | 6/2018 | Omori | A61B 1/0005 |
| 2018/0365802 A1* | 12/2018 | Onomura | G06T 5/003 |
| 2019/0139190 A1 | 5/2019 | Zhao | |
| 2020/0163538 A1* | 5/2020 | Takahashi | A61B 1/043 |
| 2020/0397266 A1* | 12/2020 | Hufford | A61B 1/0684 |

OTHER PUBLICATIONS

Kim et al, Endoscopic Raman Spectroscopy for Molecular Fingerprinting of Gastric Cancer: Principle to Implementation, Hindawi Publishing Corporation BioMed Research International vol. 2015, Article ID 670121, 9 pages, http://dx.doi.org/10.1155/2015/670121 (Year: 2015).*

Chen et al, Coherent Narrow-Band Light Source for Miniature Endoscopes, IEEE Journal of Selected Topics in Quantum Electronics, vol. 25, No. 1, Jan./Feb. 2019 7100707 (Year: 2019).*

International Search Report and Written Opinion dated Jun. 21, 2021 in counterpart International Patent Application No. PCT/US2021/025619 (15 pages, in English).

International Preliminary Report on Patentability dated Oct. 6, 2022 in International Patent Application No. PCT/US2021/025619 (8 pages).

"Demosaicing", Wikipedia, Nov. 25, 2019, Retrieved from the Internet: URL:https://en.wikipedia.org/w/index.php?title=Demosaicing &oldid=999097168 (5 pages).

* cited by examiner

IMAGE PROCESSING SYSTEMS AND METHODS OF USING THE SAME

CROSS-REFERENCE TO RELATED APPLICATIONS

This application claims the benefit of priority of U.S. Provisional Patent Application No. 63/005,832, filed Apr. 6, 2020, the entirety of which is incorporated herein by reference.

TECHNICAL FIELD

Various aspects of the disclosure relate generally to image processing systems, devices, and related methods. Examples of the disclosure relate to systems, devices, and related methods for digital chromoendoscopy, among other aspects.

BACKGROUND

Technological developments have given users of medical systems, devices, and methods, the ability to conduct increasingly complex procedures on subjects. One challenge in the field of minimally invasive surgeries is associated with visualizing target treatment sites within a subject, such as, for example, tumors or lesions located in a gastrointestinal tract of a subject. Chromoendoscopy with dye injection may facilitate detection of changes in mucosal surfaces in a luminal gastrointestinal tract. Limitations in imaging methods and devices for providing visualization of blood vessels, however, may prolong the procedure, limit its effectiveness, and/or cause injury to the patient.

SUMMARY

Aspects of the disclosure relate to, among other things, systems, devices, and methods for providing an image processing system and shifted wavelength demosaicing logic, among other aspects. Each of the aspects disclosed herein may include one or more of the features described in connection with any of the other disclosed aspects.

According to an example, a medical device includes a shaft and a sensor coupled to a distal end of the shaft and including a filter array. The sensor is configured to capture a raw image, and the filter array is configured to filter the raw image into a frame of raw pixel values that includes a plurality of first pixel values, a plurality of second pixel values, and a plurality of third pixel values. The medical device includes a processor and non-transitory computer readable medium storing demosaicing instructions that, when executed by the processor, causes the processor to exclude the plurality of first pixel values from the frame of raw pixel values. The processor generates a plurality of estimated second pixel values at locations of the plurality of excluded first pixel values and the plurality of third pixel values on the frame. The processor generates a plurality of estimated third pixel values at locations of the plurality of excluded first pixel values and the plurality of second pixel values on the frame. The processor creates a processed image having a partial-resolution frame from the plurality of second pixel values, the plurality of estimated second pixel values, the plurality of third pixel values, and the plurality of estimated third pixel values.

Any of the medial devices described herein may include any of the following features. The demosaicing instructions stored in the non-transitory computer readable medium cause the processor to detect one or more edges within the raw image and perform a sharpened enhancement of the one or more edges to increase an edge detail of the processed image. The demosaicing instructions stored in the non-transitory computer readable medium cause the processor to output a sharpened enhancement image created from performing the sharpened enhancement step and blend the sharpened enhancement image with the processed image. The demosaicing instructions stored in the non-transitory computer readable medium cause the processor to set a luminance value for each of the plurality of second pixels and the plurality of third pixels, and perform a contrast enhancement of the plurality of second pixels and the plurality of third pixels by modifying the luminance values to increase a contrast of the processed image. The demosaicing instructions stored in the non-transitory computer readable medium cause the processor to output a contrast enhancement image created from performing the contrast enhancement step, and blend the contrast enhancement image with the processed image. The demosaicing instructions stored in the non-transitory computer readable medium cause the processor to repeat all of the preceding steps until a threshold. The demosaicing instructions stored in the non-transitory computer readable medium cause the processor to receive a shifted wavelength input to determine a color pixel value of the plurality of first pixels. Further including a user interface communicatively coupled to the processor and configured to transmit a signal indicative of the shifted wavelength input to the processor. The sensor includes an RGB image sensor, and the filter array includes a red-green-blue Bayer color filter array. The plurality of first pixels includes red pixels, the plurality of second pixels includes blue pixels, and the plurality of third pixels includes green pixels. The sensor includes an RGB+Ir image sensor, and the filter array includes a red-green-blue-infrared Bayer color filter array. The plurality of first pixels includes blue pixels, the plurality of second pixels includes red pixels and green pixels, and the plurality of third pixels includes infrared pixels. The sensor includes an RGB image sensor and a monochrome sensor. Each location in the partial-resolution frame of pixels includes one captured color pixel value and one reconstructed color pixel value such that at least one color pixel value from the frame of raw pixels is excluded. Further including a light source coupled to the distal end of the shaft, wherein the light source is an optical fiber, an ultraviolet light, or a multicolor LED array. The demosaicing instructions stored in the non-transitory computer readable medium cause the processor to output the processed image of the partial-resolution frame to a display device.

According to another example, an image processing method includes capturing a raw image and filtering the raw image into a frame of raw pixels including a plurality of first pixels, a plurality of second pixels, and a plurality of third pixels. The method includes excluding at least the plurality of first pixels and generating missing second pixels along the frame at pixel locations of the plurality of excluded first pixels and the plurality of third pixels. The method includes generating missing third pixels along the frame at pixel locations of the plurality of excluded first pixels and the plurality of second pixels, and constructing a partially-sampled digital image from the plurality of second pixels, the plurality of third pixels, the generated second pixels, and the generated third pixels.

Any of the methods described herein may include any of the following steps. The method including detecting edges within the frame of raw pixels and enhancing a sharpness of the edges to increase an edge detail in the partially-sampled digital image. The method including modifying a luminance value for each of the plurality of second pixels and the plurality of third pixels to enhance a contrast of the plurality of second pixels and the plurality of third pixels in the partially-sampled digital image. The method including receiving a shifted wavelength input to determine a color pixel value of the plurality of first pixels. The frame of raw pixels further includes a plurality of fourth pixels. The method including excluding at least the plurality of fourth pixels.

According to another example, a processor and non-transitory computer readable medium storing instructions that, when executed by the processor, causes the processor to transmit light having a plurality of wavelengths from an illumination source and remove at least a subset of a plurality of pixel values detected by a digital image sensor that is communicatively coupled to the processor. The digital image sensor includes a filter array configured to filter the plurality of wavelengths of the light into the plurality of pixel values. The processor generates a plurality of estimated pixel values; and creates a processed image having a partial-resolution frame including the plurality of pixel values and the plurality of estimated pixel values, and omitting at least the subset of the plurality of pixel values from the processed image.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary aspects of the disclosure and together with the description, serve to explain the principles of the disclosure.

DETAILED DESCRIPTION

Examples of the disclosure include systems, devices, and methods for enhancing images of one or more target treatment sites within a subject (e.g., patient) by emphasizing one or more features (e.g., blood vessels, vascular system, etc.) of the target site in a processed image. Reference will now be made in detail to aspects of the disclosure, examples of which are illustrated in the accompanying drawings. Wherever possible, the same or similar reference numbers will be used through the drawings to refer to the same or like parts. The term "distal" refers to a portion farthest away from a user when introducing a device into a patient. By contrast, the term "proximal" refers to a portion closest to the user when placing the device into the subject. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal." As used herein, the terms "about," "substantially," and "approximately," indicate a range of values within +/−10% of a stated value.

Examples of the disclosure may be used to identify target sites within a subject by generating processed images having a partial-resolution frame of pixel values that visually emphasize one or more features and/or characteristics of a luminal gastrointestinal tract of the subject. Such features and/or characteristics include, for example, tumors, lesions, blood vessels, changes in a mucosal surface, and the like. In some embodiments, a medical device may include an image processing device including a processor and memory storing one or more algorithms for generating the partial-resolution frame. In embodiments, the memory may include programmable instructions in accordance with a demosaicing logic, an edge enhancement logic, and/or a contrast enhancement logic. Further, the image processing device may include a user interface operable to receive a user input thereon, such as, for example, a wavelength shifting input for filtering out at least one color pixel value prior to an interpolation and enhancement of the other color pixel values captured by an image sensor. The processed image produced by the image processing device of the medical device may include a partial-resolution frame of pixel values that may be outputted to a display device.

Examples of the disclosure may relate to devices and methods for performing various medical procedures and/or treating portions of the large intestine (colon), small intestine, cecum, esophagus, any other portion of the gastrointestinal tract, and/or any other suitable patient anatomy (collectively referred to herein as a "target treatment site"). Various examples described herein include single-use or disposable medical devices. Reference will now be made in detail to examples of the disclosure described above and illustrated in the accompanying drawings. Wherever possible, the same reference numbers will be used throughout the drawings to refer to the same or like parts.

Figure 1:
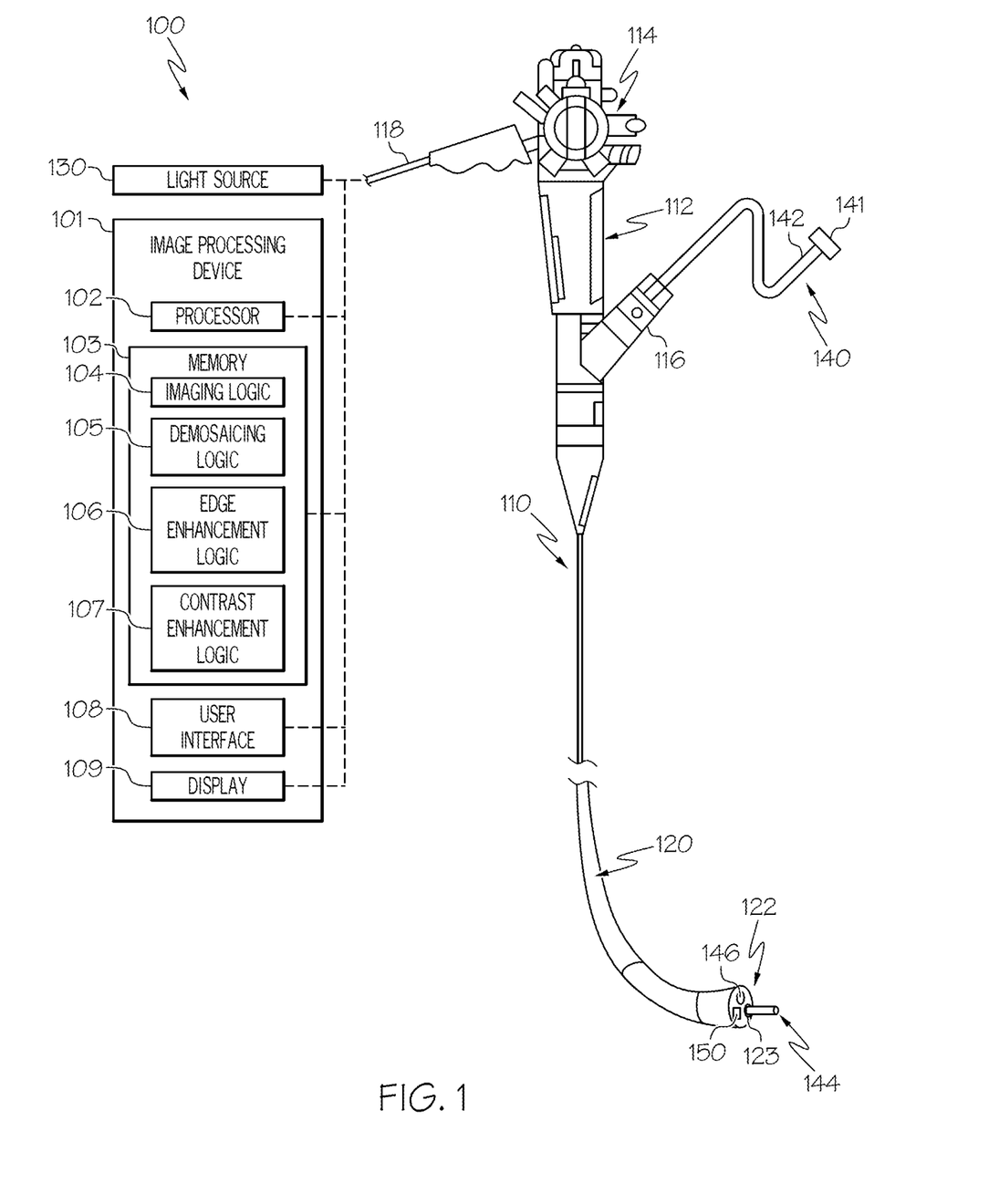
FIG. 1 is a schematic view of an exemplary medical system, according to aspects of this disclosure.

FIG. 1 shows a schematic depiction of an exemplary medical system 100 in accordance with an example of this disclosure. The medical system 100 may include one or more light sources 130, an image processing device 101, a medical instrument 110, and a medical device 140. The image processing device 101 may be communicatively coupled to the medical instrument 110 by, for example, a wired connection, a wireless connection, and the like. In examples, the image processing device 101 is a computer system incorporating a plurality of hardware components that allow the image processing device 101 to receive data (e.g., image sensor data), process information (e.g., wavelength data), and/or generate a processed image for outputting to a user of the medical system 100. Illustrative hardware components of the image processing device 101 may include at least one processor 102, at least one memory 103, at least one user interface 108, and at least one display 109.

The processor 102 of the image processing device 101 may include any computing device capable of executing machine-readable instructions, which may be stored on a non-transitory computer-readable medium, such as, for example, the memory 103 of the image processing device 101. By way of example, the processor 102 may include a controller, an integrated circuit, a microchip, a computer, and/or any other computer processing unit operable to perform calculations and logic operations required to execute a program. As described in greater detail herein, the processor 102 is configured to perform one or more operations in accordance with the instructions stored on the memory 103, such as, for example, an imaging logic 104, a demosaicing logic 105, an edge enhancement logic 106, a contrast enhancement logic 107, and the like.

Figure 2A:
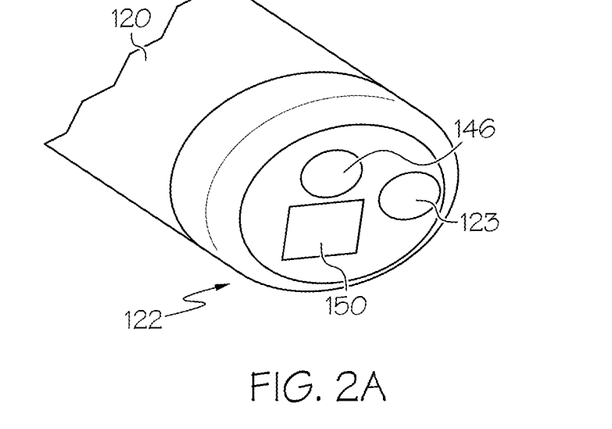
FIG. 2A is a partial perspective view of a medical device of the medical system of FIG. 1 including a sensor and a light source, according to aspects of this disclosure.
Figure 2B:
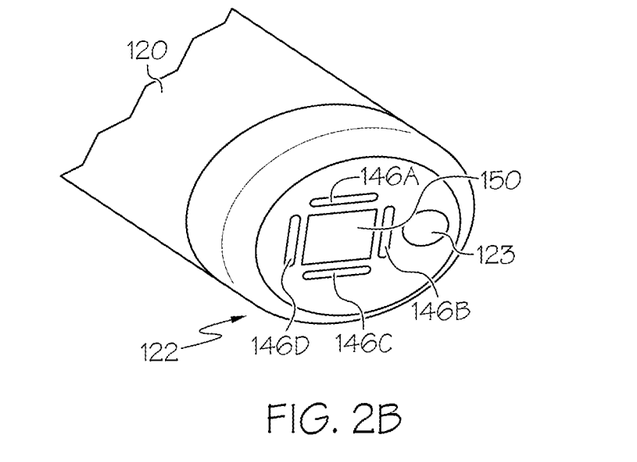
FIG. 2B is a partial perspective view of another medical device of the medical system of FIG. 1 including a sensor and a plurality of light sources, according to aspects of this disclosure.
Figure 2C:
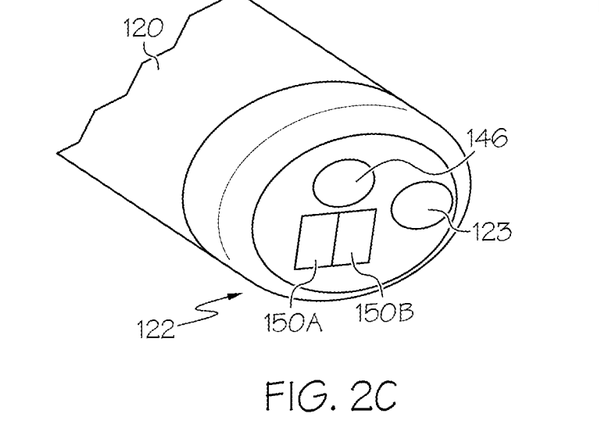
FIG. 2C is a partial perspective view of another medical device of the medical system of FIG. 1 including a pair of sensors and a light source, according to aspects of this disclosure.

Still referring to FIG. 1, the memory 103 of the image processing device 101 may include a non-transitory computer readable medium that stores machine-readable instructions thereon, such as, for example, the imaging logic 104, the demosaicing logic 105, the edge enhancement logic 106, and the contrast enhancement logic 107. The imaging logic 104 may include executable instructions that allow the medical system 100 to capture raw digital images by activating one or more components of the medical instrument 110, such as, for example, one or more image sensors 150, 150A, 150B (FIGS. 2A-2C).

Further, the demosaicing logic 105 may include executable instructions that allow the medical system 100 to process a digital image (e.g., a mosaiced image) by demosaicing the image and reconstructing missing and/or unknown pixel values in the mosaiced image. It should be understood that digital images captured by image sensors using colored filter sensor arrays may provide a raw image having various color pixel values arranged in a mosaic pattern. Each pixel array of the pattern includes only a single color pixel value such that one or more color pixel values may be omitted thereon. As described in detail herein, digital images include a two-dimensional array of pixel values, with each pixel value corresponding to a light intensity in one of a plurality of spectral bands (e.g., color pixel values) at a pixel location in the image.

Still referring to FIG. 1, the edge enhancement logic 106 may include executable instructions that allow the medical system 100 to process a mosaiced image of a target site and enhance a definition of one or more edges in the mosaiced image. It should be understood that a demosaicing process may include inherent side effects, such as, for example, degrading sharpness of one or more edges in the image. For example, a demosaicing process may attenuate a high-frequency detail of an image and/or accentuate a low-frequency detail of an image.

In this instance, chromatic fringing at the edges of sharp contrast boundaries within an image may occur, where the edges of sharp contrast boundaries may include fringe artifacts within the color pixels of the mosaiced image. As described further below, the edge enhancement logic 106 may include executable instructions that allow the medical system 100 to process a digital image (e.g., a mosaiced image) by detecting edges and increasing a detail of said edges to provide sharper definition of said images in the color pixels.

Still referring to FIG. 1, the contrast enhancement logic 107 may include executable instructions that allow the medical system 100 to process a mosaiced image of a target site and enhance a contrast of one or more pixels in the mosaiced image. It should be understood that a demosaicing process may include inherent side effects, such as, for example, diminishing a contrast of an image due to reduced color difference signals between pixels in the image.

In this instance, a resolution frame of the color pixels may lack sufficient brightness amongst the various color pixels for differentiating one or more features of the image. As described further below, the contrast enhancement logic 107 may include executable instructions that allow the medical system 100 to process a digital image (e.g., a mosaiced image) by scaling a luminance of certain color pixels and increasing a brightness of the resolution frame to provide clearer definition of said images in the color pixels.

In some embodiments, the imaging logic 104, the demosaicing logic 105, the edge enhancement logic 106, and/or the contrast enhancement logic 107 may include executable instructions that allow the medical system 100 to execute periodic image processing of a target site automatically without requiring user input. In other embodiments, the image processing device 101 may be configured to receive user inputs to initiate image processing of a target site, such as, for example, from a user interface 108 of the image processing device 101. It should be appreciated that, in some embodiments, the user interface 108 may be a device integral with the image processing device 101, and in other embodiments, the user interface 108 may be a remote device in communication (e.g., wireless, wired, etc.) with the image processing device 101.

It should be understood that various programming algorithms and data that support an operation of the medical system 100 may reside in whole or in part in the memory 103. The memory 103 may include any type of computer readable medium suitable for storing data and algorithms, such as, for example, random access memory (RAM), read only memory (ROM), a flash memory, a hard drive, and/or any device capable of storing machine-readable instructions. The memory 103 may include one or more data sets, including, but not limited to, image data from one or more components of the medical system 100 (e.g., the medical instrument 110, the medical device 140, etc.).

Still referring to FIG. 1, the medical instrument 110 may be configured to facilitate positioning one or more components of the medical system 100 relative to a subject (e.g., a patient), such as, for example, the medical device 140. In embodiments, the medical instrument 110 may be any type of endoscope, duodenoscope, gastroscope, colonoscope, ureteroscope, bronchoscope, catheter, or other delivery system, and may include a handle 112, an actuation mechanism 114, at least one port 116, and a shaft 120. The handle 112 of the medical instrument 110 may have one or more lumens (not shown) that communicate with a lumen(s) of one or more other components of the medical system 100. The handle 112 further includes the at least one port 116 that opens into the one or more lumens of the handle 112. As described in further detail herein, the at least one port 116 is sized and shaped to receive one or more instruments therethrough, such as, for example, the medical device 140 of the medical system 100.

The shaft 120 of the medical instrument 110 may include a tube that is sufficiently flexible such that the shaft 120 is configured to selectively bend, rotate, and/or twist when being inserted into and/or through a subject's tortuous anatomy to a target treatment site. The shaft 120 may have one or more lumens (not shown) extending therethrough that include, for example, a working lumen for receiving instruments (e.g., the medical device 140). In other examples, the shaft 120 may include additional lumens such as a control wire lumen for receiving one or more control wires for actuating one or more distal parts/tools (e.g., an articulation joint, an elevator, etc.), a fluid lumen for delivering a fluid, an illumination lumen for receiving at least a portion of an illumination assembly (not shown), and/or an imaging lumen for receiving at least a portion of an imaging assembly (not shown).

Still referring to FIG. 1, the medical instrument 110 may further include a tip 122 at a distal end of the shaft 120. In some embodiments, the tip 122 may be attached to the distal end of the shaft 120, while in other embodiments the tip 122 may be integral with the shaft 120. For example, the tip 122 may include a cap configured to receive the distal end of the shaft 120 therein. The tip 122 may include one or more openings that are in communication with the one or more lumens of the shaft 120. For example, the tip 122 may include a working opening 123 through which the medical device 140 may exit from a working lumen of the shaft 120. It should be appreciated that other one or more openings at the tip 122 of the shaft 120 are not shown. The actuation mechanism 114 of the medical instrument 110 is positioned on the handle 112 and may include one or more knobs, buttons, levers, switches, and/or other suitable actuators. The actuation mechanism 114 is configured to control at least a deflection of the shaft 120 (e.g., through actuation of a control wire).

The medical device 140 of the medical system 100 may include a catheter having a longitudinal body 142 between a proximal end 141 of the medical device 140 and a distal end 144 of the medical device 140. The longitudinal body 142 of the medical device 140 may be flexible such that the medical device 140 is configured to bend, rotate, and/or twist when being inserted into a working lumen of the medical instrument 110. The medical device 140 may include a handle at the proximal end 141 of the longitudinal body 142 that may be configured to move, rotate, and/or bend the longitudinal body 142. Further, the handle at the proximal end 141 of the medical device 140 may define one or more ports (not shown) sized to receive one or more tools through the longitudinal body 142 of the medical device 140.

Still referring to FIG. 1, the medical instrument 110 may be configured to receive the medical device 140 via the at least one port 116, through the shaft 120 via a working lumen, and to the working opening 123 at the tip 122. In this instance, the medical device 140 may extend distally out of the working opening 123 and into a surrounding environment of the tip 122, such as, for example, at a target treatment site of a subject as described in further detail below. The distal end 144 of the medical device 140 may extend distally from the tip 122 in response to a translation of the longitudinal body 142 through the working lumen of the shaft 120. The medical device 140 may include one or more end effectors (not shown) at the distal end 144 of the longitudinal body 142, for performing one or more operations at a target treatment site.

The medical instrument 110 may be further configured to receive the one or more light sources 130 through the shaft 120 via at least one of the lumens of the medical instrument 110 for connection to the optical fiber 146. In the example, the one or more light sources 130 are shown as a separate component from the image processing device 101 such that the light sources 130 are coupled to the medical instrument 101 separately from the image processing device (e.g., via a cable). It should be appreciated that, in other embodiments, the one or more light sources 130 may be included on the image processing device 101 such that the light sources 130 may be communicatively coupled to the medical instrument 110 with the image processing device 101.

Referring now to FIGS. 2A-2C, the tip 122 of the medical instrument 110 is depicted in accordance with one or more examples of this disclosure. Referring initially to FIG. 2A, in one embodiment, the tip 122 of the medical instrument 110 may include an optical fiber 146 and an image sensor 150 at the tip 122. In the example, the optical fiber 146 may be coupled to the one or more light sources 130 of the medical system 100, such that each of the one or more light sources 130 may transmit light through the single, optical fiber 146. Although not shown, it should be appreciated that multiple light sources 130 may be coupled to the optical fiber 146 via a fiber splitter/combiner. The optical fiber 146 of the medical instrument 110 may be configured and operable to deliver various amplitudes of light, from the one or more light sources 130, distally from the tip 122 of the shaft 120. In some embodiments, the optical fiber 146 may be configured to deliver white light, ultraviolet light, near-infrared (NIR) light, and/or various other wavelengths within or beyond a visible spectrum.

Still referring to FIG. 2A, the image sensor 150 of the medical instrument 110 may be communicatively coupled to the image processing device 101 of the medical system 100, such as, for example, via a wired connection, a wireless connection, and/or the like. The image sensor 150 of the medical instrument 110 may be configured and operable to capture a raw image (e.g., a digital image) of a surrounding environment of the tip 122 of the shaft 120. In some embodiments, the image sensor 150 may include an image sensor, such as, for example, an RGB (i.e., red-green-blue) digital sensor, an RGB-Ir (i.e., red-green-blue-infrared) digital sensor, a monochrome sensor, and/or the like. As described in further detail herein, the image sensor 150 may include one or more components for filtering colors from white light, ultraviolet light, near-infrared light, and/or other wavelengths within or beyond a visible spectrum.

In other embodiments, referring now to FIG. 2B, the medical instrument 110 may include a multicolor LED assembly at the tip 122 of the shaft 120. In this instance, the multicolor LED assembly may include one or more light-emitting diodes (hereinafter LEDs) 146A, 146B, 146C, 146D disposed in an annular array about the image sensor 150. Each of the LEDs 146A, 146B, 146C, 146D may be configured and operable to transmit a different light wavelength and/or amplitude (e.g., color) relative to one another. It should be understood that different illumination sources may generate different spectra. It should be appreciated that the LEDs 146A, 146B, 146C, 146D of the medical instrument 110 may include additional and/or fewer diodes on the tip 122 than those shown and described herein without departing from a scope of this disclosure.

In other embodiments, referring now to FIG. 2C, the medical instrument 110 may include a multi sensor assembly at the tip 122 of the shaft 120. In this instance, the multi sensor assembly may include a color image sensor 150A and a monochrome image sensor 150B. As described in further detail herein, the color image sensor 150A may be configured and operable to capture a portion of incoming light at each individual pixel location of the color image sensor 150A depending on a color of the incoming light. In some embodiments, the color image sensor 150A may include, for example, an RGB (red-green-blue digital sensor), an RGB-Ir (red-green-blue-infrared) digital sensor, and the like. As further described herein, the monochrome image sensor 150B may be configured and operable to fully capture all incoming light at each individual pixel location of the monochrome sensor 150B irrespective of a color of the incoming light.

Figure 3:
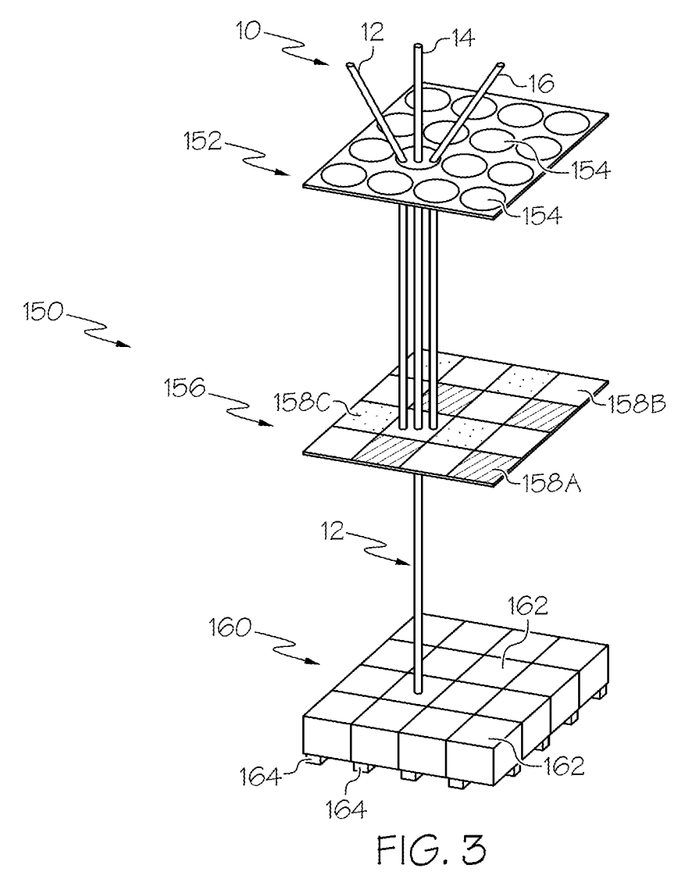
FIG. 3 is a schematic view of an exemplary image sensor of the medical device of FIG. 2A, according to aspects of this disclosure.

Referring now to FIG. 3, the image sensor 150 of the medical instrument 110 may include an exterior surface 152 having a plurality of micro lenses 154 disposed thereon. In some examples, the exterior surface 152 and/or the plurality of micro lenses 154 may be formed of glass, plastic, and/or other transparent materials. The image sensor 150 may be a color image sensor including a color filter array 156 disposed relatively underneath the exterior surface 152. The color filter array 156 may include an optical filter device having a plurality of color pixel locations 158A, 158B, 158C arranged in a predefined pattern. In the example, each of the plurality of micro-lenses 154 may be positioned in alignment with at least one of the plurality of color pixel locations 158A, 158B, 158C of the color filter array 156 disposed underneath the exterior surface 152.

In some embodiments, the color filter array 156 may include a plurality of first color pixel locations 158A, a plurality of second color pixel locations 158B, and/or a plurality of third color pixel locations 158C. The plurality of color pixel locations 158A, 158B, 158C may be arranged along the color filter array 156 in a mosaic pattern, such as, for example, a Bayer pattern. In the example, the plurality of first color pixel locations 158A may include red-color filter, the plurality of second color pixel locations 158B may include green-colored filter, and the plurality of third color pixel locations 158C may include blue-colored filter. In other embodiments, the plurality of color pixels 158A, 158B, 158C may include various other suitable colored filters and/or patterns than those shown and described herein. For example, in embodiments where the image sensor 150 includes an RGB-Ir sensor, it should be understood that the color filter array 156 may additionally include a plurality of fourth color pixel locations corresponding to an infrared-colored filter.

Still referring to FIG. 3, the color filter array 156 of the image sensor 150 may be configured and operable to selectively transmit one or more wavelengths 12, 14, 16 (e.g., light intensities, spectral bands, colors, etc.) of a light beam 10. For example, each of the color pixel locations 158A, 158B, 158C is configured to allow delivery and/or passage of a partial portion of the light beam 10 (e.g., at least one wavelength 12, 14, 16) therethrough depending on the colored filter at said color pixel location 158A, 158B, 158C. Accordingly, only a single color component (e.g., color pixel value) may be measured by the image sensor 150 at each color pixel location 158A, 158B, 158C. As described further herein, a color pixel value may include a quantity of electrical energy in a colored range of the spectrum (e.g., red range, green range, blue range, etc.).

In the example, each of the plurality of color pixel locations 158A, 158B, 158C may permit only one wavelength 12, 14, 16 of the light beam 10 to pass through the color filter array 156. The image sensor 150 may further include a photosensor array 160 disposed relatively underneath the color filter array 156, such that the color filter array 156 of the image sensor 150 may be positioned between the exterior surface 152 and the photosensor array 160. The photosensor array 160 of the image sensor 150 may include a photodiode (e.g., semiconductor device) having a plurality of photosites 162 and a circuitry 164 communicatively coupled to the plurality of photosites 162.

Still referring to FIG. 3, the plurality of photosites 162 are arranged in an array (e.g., grid) with each of the plurality of photosites 162 positioned in alignment with at least one of the plurality of color pixel locations 158A, 158B, 158C of the color filter array 156 disposed over the photosensor array 160. The photosensor array 160 may be configured and operable to convert the light beam 10 received through the outer surface 152 and the color filter array 156 into an electrical current. In the example, the electrical current may be generated by the photosensor array 160 when photons from the received light are absorbed in the plurality of photosites 162.

In the example, each of the plurality of photosites 162 may be configured to measure a quantity of only one color pixel value (e.g., red, green, blue) in the incoming light 10 at a location of the photosite 162 along a surface of the photosensor array 160. Accordingly, the plurality of photosites 162 may capture the incoming light 10 and may generate an electrical signal which is quantified and stored as a numerical value in a resulting processed image file. It should be appreciated that the photosensor array 160 may include various suitable shapes, sizes, and/or configurations other than that shown and described herein. In other embodiments, the image sensor 150 may be a monochrome sensor (e.g., the monochrome sensor 150B) such that the color filter array 156 shown and described above may be omitted entirely from between the exterior surface 152 and the photosensor array 160. In this instance, each photosite 162 along the photosensor array 160 may be operable to receive, capture, and absorb all three wavelengths 12, 14, 16 of the light beam 10.

Figure 4:
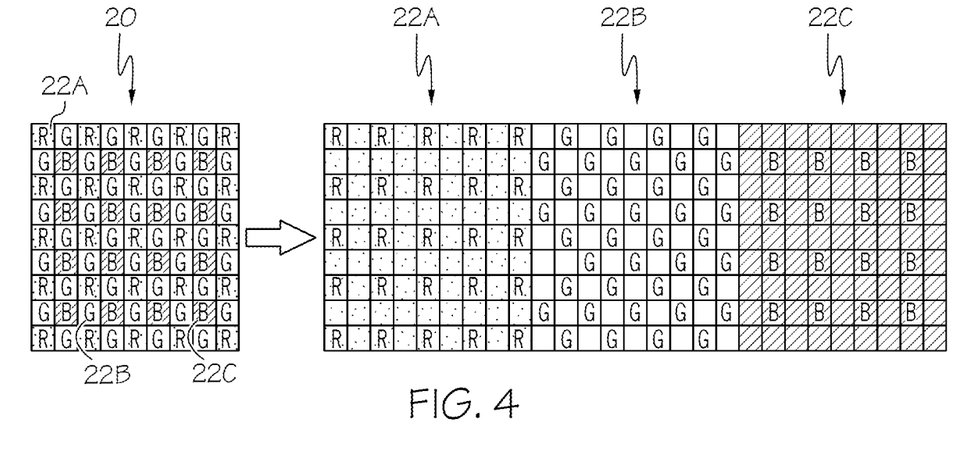
FIG. 4 is a schematic view of a frame of raw pixel data received from an image captured by the image sensor of FIG. 3, according to aspects of this disclosure.
Figure 5:
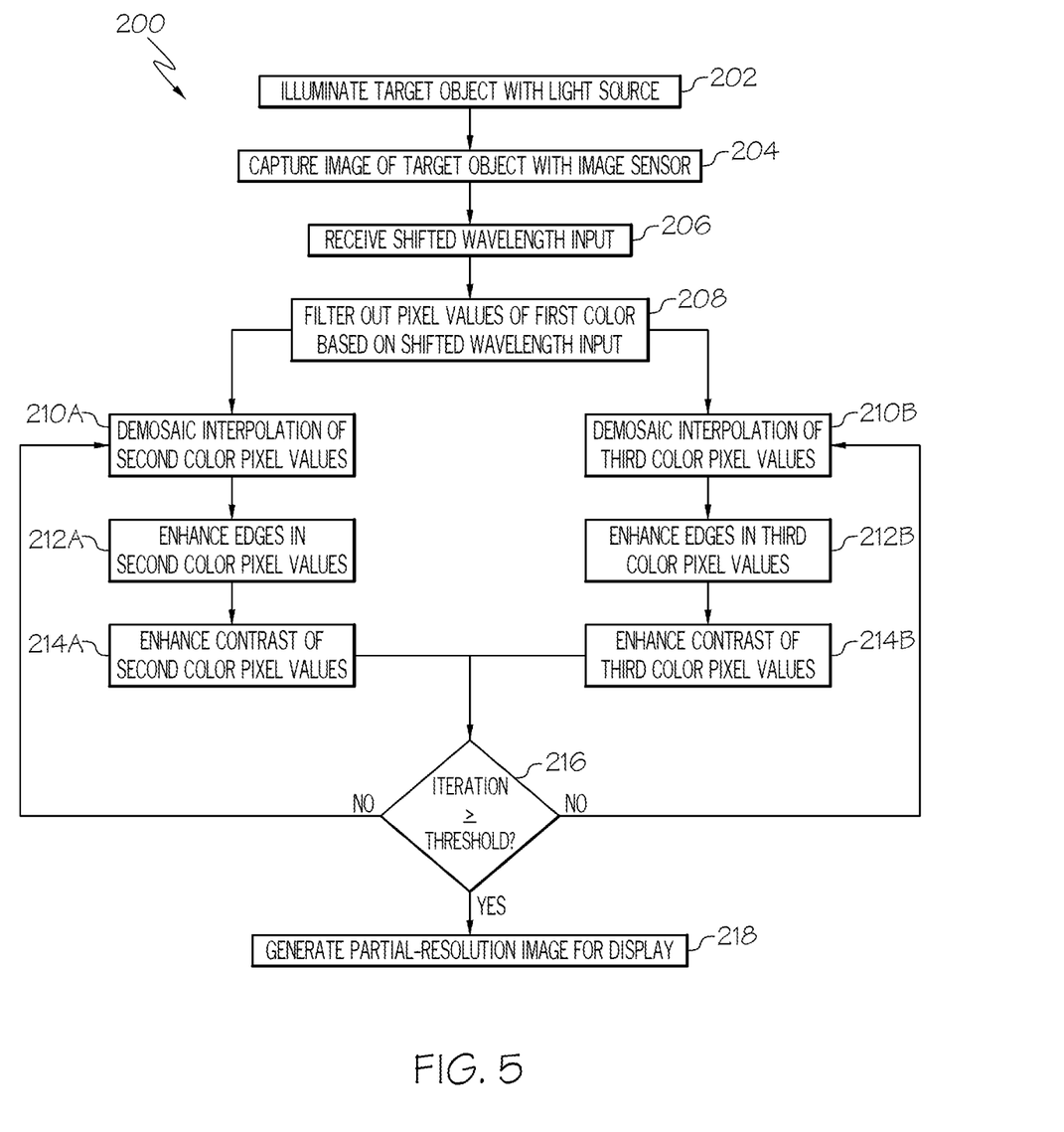
FIG. 5 is a block diagram of an exemplary method of imaging a target site with the medical system of FIG. 1, according to aspects of this disclosure.

Referring now to FIGS. 3-4 in conjunction with the flow diagram of FIG. 5, an exemplary method 200 of using the medical system 100 to generate a processed image of a target site is schematically depicted. The depiction of FIGS. 3-5 and the accompanying description below is not meant to limit the subject matter described herein to a particular method.

Initially, referring to FIG. 1, the medical instrument 110 of the medical system 100 may be inserted within a subject's body (not shown) to position the tip 122 adjacent to a target site. For example, the shaft 120 may be guided through a digestive tract of the subject (e.g., patient) by inserting the tip 122 into a nose or mouth (or other suitable natural body orifice) of the subject's body and traversed through a gastrointestinal tract of the subject's body (e.g., an esophagus, a stomach, a small intestine, etc.) until reaching the target site. It should be appreciated that a length of the shaft 120 may be sufficient so that a proximal end of the medical instrument 110 (including the handle 112) is external of the subject while the tip 122 of the medical instrument 110 is internal to the subject's body. While this disclosure relates to the use of the medical system 100 in a digestive tract of a subject, it should be understood that the features of this disclosure could be used in various other locations (e.g., other organs, tissue, etc.) within a subject's body.

Additionally, with the medical instrument 110 received within the subject and the tip 122 of the shaft 120 located relatively adjacent to the target site, the medical device 140 may be received within the medical instrument 110 via the at least one port 116. In this instance, the longitudinal body 142 of the medical device 140 is translated through the shaft 120 via at least one of the lumens of the shaft 120 (e.g., a working lumen). The distal end 144 of the longitudinal body 142 may be extended distally from the tip 122 of the shaft 120 via the working opening 123 which is in communication with a working lumen of the shaft 120. It should be appreciated that this step may be optional such that receiving the medical device 140 through the medical instrument 110 may be performed at various other steps in the method 200 and/or omitted entirely. The tip 122 may be positioned adjacent to and facing the target treatment site.

Referring to FIG. 5, at step 202, the one or more target objects may be illuminated by the medical instrument 110 in response to the processor 102 of the image processing device 101 executing the imaging logic 104 to activate the one or more light sources 130. In an example with the medical instrument 110 including the optical fiber 146 (FIG. 2A) and/or the multicolor LED assembly 146A, 146B, 146C, 146D (FIG. 2B), light from the one or more light sources 130 may be emitted from the medical instrument 110 at the tip 122 to illuminate the target object.

At step 204, with the target object illuminated by light from the medical instrument 110, the image sensor 150 may be activated by the processor 102 executing the imaging logic 104 to capture one or more raw digital images of the target object. It should be understood that the processor 102 of the image processing device 101 may be communicatively coupled to the image sensor 150 of the medical instrument 110 via the circuitry 164. For example, referring back to FIG. 3, the light 10 transmitted to the target object by the optical fiber 146 and/or the multicolor LED assembly 146A, 146B, 146C, 146D may reflect off the target object and be received at the image sensor 150. In this instance, the plurality of wavelengths 12, 14, 16 of the light 10 may be received through one or more of the plurality of micro lenses 154 on the exterior surface 152.

The plurality of wavelengths 12, 14, 16 may be received at one or more corresponding color pixel locations 158A, 158B, 158C of the color filter array 156, such as those aligned with the micro lenses 154 that received the light beam 10 therethrough. One or more of the plurality of wavelengths 12, 14, 16 of the light 10 at each of the plurality of color pixel locations 158A, 158B, 158C may be inhibited (e.g., filtered, excluded, omitted, blocked) from passing through the color filter array 156 dependent on a color filter at the color pixel location 158A, 158B, 158C. Thus, a color filter configuration (e.g., red, green, blue etc.) of the color pixel location 158A, 158B, 158C receiving the light 10 is determinative of which of the wavelengths 12, 14, 16 (e.g., red, blue, green, etc.) is permitted to pass through the color filter array 156 at said location.

Accordingly, it should be understood that each of the color pixel locations 158A, 158B, 158C may only permit about one-third (e.g., 33%) of the incoming light 10 to pass through to the photosensor array 160 at said location. For example, at each of the plurality of first color pixel locations 158A (e.g., red-colored filters), only the wavelength 12 (e.g., red range of light spectrum) of the light 10 is permitted through the color filter array 156, such that the wavelengths 14, 16 (e.g., blue and green, respectively) may be filtered by the color filter array 156 at said first color pixel locations 158A. It should be appreciated that, in the embodiment, the plurality of second color pixel locations 158B (e.g., green-colored filters) may be configured to permit the wavelength 14 (e.g., green range of light spectrum) and the plurality of third color pixel locations 158C (e.g., blue-colored filters) may be configured to permit the wavelength 16 (e.g., blue range of light spectrum), respectively.

Still referring to FIG. 3, the individual wavelengths 12, 14, 16 of the light 10 passing through the color filter array 156 may be detected along the photosensor array 160 and absorbed by one or more of the plurality of photosites 162 (i.e., those aligned with the color pixel locations 158A, 158B, 158C that received the light beam 10 therethrough). In this instance, the portion of the light 10 absorbed by each of the plurality of photosites 162 may be converted into an electrical current. The raw digital image captured by the image sensor 150 may include a quantitative recording of light energy measured at each grid location of the photosites 162 along the photosensor array 160, with each photosite 162 configured to determine a color pixel value of the wavelength 12, 14, 16 received thereon.

In this instance, the processor 102 of the image processing device 101, when executing the imaging logic 104, may cause the photosensor array 160 to transmit an electrical signal of the color pixel values to the image processing device 101, such as, for example, via the circuitry 164. The electrical signal of the color pixel values may be stored in the memory 103 of the image processing device 101 and utilized by the demosaicing logic 105, the edge enhancement logic 106, and/or the contrast enhancement logic 107 to generate a processed image.

Referring to FIG. 5, at step 206, a shifted wavelength input may be inputted by a user of the medical system 100, such as, for example, via the user interface 108 of the image processing device 101. The shifted wavelength input may include an identification of one or more light wavelengths, amplitudes, color pixel values, and/or the like, for modifying a demosaicing process of the raw digital image captured by the image sensor 150. It should be appreciated that, in some embodiments, step 206 may occur prior to steps 202 and 204 and/or be automatically preprogrammed in the memory 103 of the image processing device 101 such that the method 200 may proceed to step 208 with the shifted wavelength input predetermined.

Referring now to FIG. 4, the raw digital image received at the image processing device 101 may include a frame (e.g., grid) of raw pixels 20 formed of a plurality of color pixel values 22A, 22B, 22C measured by the image sensor 150. It should be understood that each of the grid locations along the frame of raw pixels 20 may correspond to a location of the photosites 162 on the photosensor array 160. Thus, each of the grid locations on the frame of raw pixels 20 includes at least one of a first color pixel value 22A, a second color pixel value 22B, or a third color pixel value 22C, based on a relative position of the grid location to the color pixel locations 158A, 158B, 158C of the color filter array 156 that the photosites 162 received the wavelengths 12, 14, 16 through.

At step 208, the processor 102 may isolate the frame of raw pixels 20 by the color pixel values 22A, 22B, 22C and filter out (e.g., exclude) at least one of the first color pixel value 22A, the second color pixel value 22B, or the third color pixel value 22C based on the shifted wavelength input received at step 206. In other words, the image processing device 101 is configured to shift a demosaicing process of the raw digital image captured by the image sensor 150 to a subset of the color pixel values 22A, 22B, 22C from the plurality of color pixel values 22A, 22B, 22C in the frame of raw pixel values 20.

Accordingly, as described in detail below, a demosaicing process (step 210A, 210B), edge enhancement process (step 212A, 212B), and/or contrast enhancement process (step 214A, 214B) of the raw digital image is executed on only a partial portion of the frame of raw pixel values 20 included in the raw digital image captured by the image sensor 150. In the example, processor 102 of the image processing device 101 removes the plurality of first color pixel values 22A in accordance with the shifted wavelength input such that a resulting processed image generated by the image processing device 101 includes a partial-resolution frame of pixels.

For example, still referring to FIG. 5, at step 210A, the processor 102 may perform a demosaicing process of the plurality of second color pixel values 22B at step 210A (when executing the demosaicing logic 105) to compute an inferred measurement of the second color pixel values 22B (e.g., green) at grid locations along the frame of raw pixels 20 that did not receive the wavelength 14 (e.g., green), such as, for example, grid locations receiving the wavelength 12 (e.g., red) and the wavelength 16 (e.g., blue). The processor 102 may infer measurements of unknown second color pixel values 22B at grid locations on the frame of raw pixel values 20 that did not receive the wavelength 14 by interpolating from the measurements of known second color pixel values 22B.

In the example, the processor 102 executing the demosaicing logic 105 interpolates the missing second color pixel values 22B from adjacent (e.g., neighboring) grid locations that include a measured second color pixel value 22B. The processor 102 determines a measurement of the unknown second color pixel values 22B from neighboring grid locations that received the wavelength 14. It should be understood that the processor 102 may execute the demosaicing logic 105 to reconstruct unknown and/or missing third color pixel values 22C along the frame of raw pixel values 20 at step 210B in a substantially similar manner as that described above with respect to step 210A.

Still referring to FIG. 5, at step 212A, the processor 102 of the image processing device 101 may execute the edge enhancement logic 106 to further reconstruct the raw digital image captured by the image sensor 150. In the example, the edge enhancement logic 106, when executed by the processor 102, may enhance a detail and/or definition of one or more edges in the frame of raw pixel values 20. For example, the processor 102 may detect a location of one or more edges within each grid location in the frame of raw pixel values 20 and minimize a noise level surrounding the edge(s) by adjusting one or more of the plurality of second color pixel values 22B at the grid location. In some embodiments, the processor 102 may increase a sharpness of one or more edges in a grid location by enhancing a gradient (e.g., magnitude) of the plurality of second color pixel values 22B.

It should be understood that the processor 102 may execute the edge enhancement logic 106 to reconstruct edges of the digital image by adjusting one or more of the plurality of third color pixel values 22C along the frame of raw pixel values 20 at step 212B in a substantially similar manner as that described above with respect to step 212A. It should be appreciated that, in other embodiments, various other suitable edge enhancement processes may be included in the edge enhancement logic 106 and executed by the processor 102.

Still referring to FIG. 5, at step 214A, the processor 102 of the image processing device 101 may execute the contrast enhancement logic 107 to further reconstruct the raw digital image captured by the image sensor 150. In the example, the contrast enhancement logic 107, when executed by the processor 102, may enhance a contrast of the representation in the frame of raw pixel values 20. For example, the processor 102 may increase a brightness component (e.g., a luminance) of one or more of the plurality of second color pixel values 22B within each grid location in the frame of raw pixel values 20. In some embodiments, the processor 102 may modify a brightness of one or more grid locations within the frame of raw pixel values 20 by scaling down the second color pixel values 22B located therein to reduce the contrast contribution provided by the second color pixel values 22B.

It should be understood that the processor 102 may execute the contrast enhancement logic 107 to increase a local contrast of the digital image by adjusting one or more of the plurality of third color pixel values 22C along the frame of raw pixel values 20 at step 214B in a substantially similar manner as that described above with respect to step 214A. It should be appreciated that, in other embodiments, various other suitable contrast enhancement processes may be included in the contrast enhancement logic 107 and executed by the processor 102.

Still referring to FIG. 5, at step 216, the processor 102 of the image processing device 101 may determine whether a current iteration of the demosaicing process (steps 210A, 210B), the edge enhancement process (steps 212A, 212B), and the contrast enhancement process (steps 214A, 214B) is equal to or greater than a predetermined and/or dynamic iterative threshold. In some embodiments, the predetermined iterative threshold may be predefined and stored in the memory 103 of the image processing device 101, or selectively inputted by a user of the medical system 100.

In other embodiments, the iterative threshold may be dynamically determined by the processor 102 based on one or more factors, including, for example, peak definition, contrast, and visibility values from an initial conversion of the digital image through the demosaicing, edge enhancement, and contrast enhancement processes. In this instance, data indicative of an initial state of the raw pixel values 20 (e.g., a histogram of the frame) may be analyzed upon completion of a first iteration by the processor 102 and a peak value may be determined for definition, contrast, and visibility characteristics. Accordingly, the processor 102 may continuously determine a present definition, contrast, and visibility of the digital image upon completion of each iteration of the processes relative to the initial peak values (i.e. the dynamic iterative threshold).

In response to the processor 102 determining that the current iteration of the method 200 is less than the predetermined (or dynamic) threshold at step 216, the image processing device 101 may be configured and operable to return to steps 210A, 210B to execute one or more of the demosaicing, edge enhancement, and/or contrast enhancement processes. In response to the processor 102 determining that the current iteration of the method 200 is at least equal to or greater than the predetermined (or dynamic) threshold at step 216, the image processing device 101 may be configured and operable to produce an interpolated output image. It should be appreciated that an image with improved definition, contrast, and/or visibility may be provided in response to an iterative enhancement of the frame of raw pixel values 20 initially captured by the image sensor 150.

Still referring to FIG. 5, at step 218, the processor 102 of the image processing device 101 may generate a processed image resulting from the processes of the method 200 shown and described herein. In the example, the output image may include a partial-resolution frame of color pixel values, such as, for example, the plurality of second color pixel values 22B and the plurality of third color pixel values 22C. Accordingly, the digital image generated by the processor 102 of the image processing device 101 may omit at least the plurality of first color pixel values 22A from one or more of the grid locations of the frame of raw pixel values 20 initially captured by the image sensor 150. In the example, the generated image excludes the first color pixel values 22A in each of the grid locations of the frame of raw pixel values 20 such that the image processing device 101 produces a partial-resolution image.

With the display 109 of the medical system 100 communicatively coupled to the processor 102 of the image processing device 101, the processor 102 may be operable to transmit the partial-resolution image to the display 109 for viewing by a user of the medical system 100. In some examples, the medical system 100 may be configured and operable to continuously execute the method 200 shown and described herein such that the display 109 may output a plurality of partial-resolution images to provide a continuous (e.g., live, real-time, etc.) imaging of the one or more target objects.

It should be appreciated that removing at least one of the plurality of color pixel values 22A, 22B, 22C initially captured in the frame of raw pixel values 20 (by the image sensor 150) from the processed image may facilitate a differentiation of one or more features and/or structures (e.g., target objects) at the target treatment site. For example, improving a distinguishability of blood vessels from surrounding tissues may be provided in response to the processor 102 filtering out at least one of the color pixel values 22A, 22B, 22C in accordance with the shifted wavelength input at step 206. In some examples, a predominant color for one or more target objects may be substantially similar to one another, such as tissues and blood vessels being generally displayed as red, thereby minimizing a differentiation of said features in a produced image. In this instance, emphasizing blue and/or green color pixels (e.g., the second color pixel values 22B and the third color pixel values 22C, respectively) may enhance a differentiation of said features.

Additionally, it should be understood that one or more color components may include lower contrast (e.g., red) compared to one or more other color components (e.g., green, blue) within a target treatment site. Excluding one or more of the color components from the resulting digital image, such as, the first color pixel values 22A (e.g., red) may enhance a vasculature of a subject as only the second color pixel values 22B (e.g., blue) and the third color pixel values 22C (e.g., green) may be maintained from the frame of raw pixel values 20.

In embodiments where the optical fiber 146 of the medical device 140 is operable to generate ultraviolet light, the medical system 100 may be configured to produce a partial-resolution frame capable of differentiating desirous (e.g., healthy) tissue from undesirous (e.g., unhealthy) tissue as said tissues may fluoresce at different colors under ultraviolet illumination. In the example, the shifted wavelength input of step 206 may include the first color pixel values 22A (e.g., red) and the third color pixel values 22C (e.g., green), such that only the second color pixel values 22B (e.g., blue) may be included in the resulting, processed image.

In embodiments where the image sensor 150 of the medical instrument 110 includes an RGB-Ir sensor, the frame of raw pixel values 20 detected and captured by the image sensor may include the plurality of first color pixel values 22A (e.g., red), the plurality of second color pixel values 22B (e.g., blue), the plurality of third color pixel values 22C (e.g., green), and a plurality of fourth color pixel values (e.g., infrared) that are beyond the visible spectrum and closer to the infrared spectrum. In this instance, the medical system 100 may be configured to produce a partial-resolution frame capable of enhancing relatively darker regions within a target treatment site (e.g., a bodily lumen) by emphasizing the first color pixel values 22A, the third color pixel values 22C, and/or the fourth color pixel values. Accordingly, the shifted wavelength input of step 206 may include the second color pixel values 22B (e.g., blue) for removal from the processed image.

In embodiments where the tip 122 of the shaft 120 includes the color image sensor 150A (e.g., RGB-Ir sensor) and the monochrome image sensor 150B, the image processing device 101 may be configured to generate a partial-resolution image captured by the color image sensor 150A while further enhancing a contrast of relatively darker areas within the frame of raw pixel values 20 with the monochrome image sensor 150B. In this instance, the monochrome image sensor 150B may be sensitive to a near-infrared wavelength illuminated in the light 10 such that the fourth color pixel values (e.g., infrared) may be easily detected. It should be appreciated that providing one or more materials in the target treatment site may facilitate a visualization of the one or more target objects by the monochrome image sensor 150B, such as, for example, a fluorescent dye.

Each of the aforementioned systems, devices, assemblies, and methods may be used to generate a partial-resolution frame of pixel values of a subject. By providing a medical device including an image processing system storing a shifted wavelength demosaicing logic, a user may enhance a visualization of one or more features and/or characteristics of a target site within a subject during a procedure without requiring manipulation of a light source. The medical device may allow a user to accurately identify a location of a target site, thereby reducing overall procedure time, increasing efficiency of procedures, and avoiding unnecessary harm to a subject's body caused by inaccurately locating target objects in the target treatment site.

It will be apparent to those skilled in the art that various modifications and variations may be made in the disclosed devices and methods without departing from the scope of the disclosure. It should be appreciated that the disclosed devices may include various suitable computer systems and/or computing units incorporating a plurality of hardware components, such as, for example, a processor and non-transitory computer-readable medium, that allow the devices to perform one or more operations during a procedure in accordance with those described herein. Other aspects of the disclosure will be apparent to those skilled in the art from consideration of the specification and practice of the features disclosed herein. It is intended that the specification and examples be considered as exemplary only.

We claim:

1. A medical device, comprising:
  a shaft;
  a sensor coupled to a distal end of the shaft and including a filter array, wherein the sensor is configured to capture a raw image, and the filter array is configured to filter the raw image into a frame of raw pixel values that includes a plurality of first pixel values, a plurality of second pixel values, and a plurality of third pixel values; and
  a processor and non-transitory computer readable medium storing demosaicing instructions that, when executed by the processor, causes the processor to:
    exclude the plurality of first pixel values from the frame of raw pixel values;
    generate a plurality of estimated second pixel values at locations of the plurality of excluded first pixel values and the plurality of third pixel values on the frame;
    generate a plurality of estimated third pixel values at locations of the plurality of excluded first pixel values and the plurality of second pixel values on the frame; and
    create a processed image having a partial-resolution frame from the plurality of second pixel values, the plurality of estimated second pixel values, the plurality of third pixel values, and the plurality of estimated third pixel values.

2. The medical device of claim 1, wherein the demosaicing instructions stored in the non-transitory computer readable medium cause the processor to:
  detect one or more edges within the raw image; and
  perform a sharpened enhancement of the one or more edges to increase an edge detail of the processed image.

3. The medical device of claim 2, wherein the demosaicing instructions stored in the non-transitory computer readable medium cause the processor to:
  output a sharpened enhancement image created from performing the sharpened enhancement step; and
  blend the sharpened enhancement image with the processed image.

4. The medical device of claim 3, wherein the demosaicing instructions stored in the non-transitory computer readable medium cause the processor to:
  set a luminance value for each of the plurality of second pixels and the plurality of third pixels; and
  perform a contrast enhancement of the plurality of second pixels and the plurality of third pixels by modifying the luminance values to increase a contrast of the processed image.

5. The medical device of claim 4, wherein the demosaicing instructions stored in the non-transitory computer readable medium cause the processor to:
  output a contrast enhancement image created from performing the contrast enhancement step; and
  blend the contrast enhancement image with the processed image.

6. The medical device of claim 5, wherein the demosaicing instructions stored in the non-transitory computer readable medium cause the processor to:
  repeat all of the preceding steps until a threshold.

7. The medical device of claim 1, wherein the demosaicing instructions stored in the non-transitory computer readable medium cause the processor to:
  receive a shifted wavelength input to determine a color pixel value of the plurality of first pixels.

8. The medical device of claim 7, further including a user interface communicatively coupled to the processor and configured to transmit a signal indicative of the shifted wavelength input to the processor.

9. The medical device of claim 1, wherein the sensor includes an RGB image sensor, and the filter array includes a red-green-blue Bayer color filter array; and
  wherein the plurality of first pixels includes red pixels, the plurality of second pixels includes blue pixels, and the plurality of third pixels includes green pixels.

10. The medical device of claim 1, wherein the sensor includes an RGB+Ir image sensor, and the filter array includes a red-green-blue-infrared Bayer color filter array; and
  wherein the plurality of first pixels includes blue pixels, the plurality of second pixels includes red pixels and green pixels, and the plurality of third pixels includes infrared pixels.

11. The medical device of claim 1, wherein the sensor includes an RGB image sensor and a monochrome sensor.

12. The medical device of claim 1, wherein each location in the partial-resolution frame of pixels includes one captured color pixel value and one reconstructed color pixel value such that at least one color pixel value from the frame of raw pixels is excluded.

13. The medical device of claim 1, further including a light source coupled to the distal end of the shaft, wherein the light source is an optical fiber, an ultraviolet light, or a multicolor LED array.

14. The medical device of claim 1, wherein the demosaicing instructions stored in the non-transitory computer readable medium cause the processor to:
  output the processed image of the partial-resolution frame to a display device.

15. An image processing method, comprising:
  capturing a raw image;
  filtering the raw image into a frame of raw pixels including a plurality of first pixels, a plurality of second pixels, and a plurality of third pixels;
  excluding at least the plurality of first pixels;
  generating missing second pixels along the frame at pixel locations of the plurality of excluded first pixels and the plurality of third pixels;
  generating missing third pixels along the frame at pixel locations of the plurality of excluded first pixels and the plurality of second pixels; and
  constructing a partially-sampled digital image from the plurality of second pixels, the plurality of third pixels, the generated second pixels, and the generated third pixels.

16. The method of claim 15, further comprising detecting edges within the frame of raw pixels and enhancing a sharpness of the edges to increase an edge detail in the partially-sampled digital image.

17. The method of claim 15, further comprising modifying a luminance value for each of the plurality of second pixels and the plurality of third pixels to enhance a contrast of the plurality of second pixels and the plurality of third pixels in the partially-sampled digital image.

18. The method of claim 15, further comprising receiving a shifted wavelength input to determine a color pixel value of the plurality of first pixels.

19. The method of claim 15, wherein the frame of raw pixels further includes a plurality of fourth pixels; and
  the method further comprising excluding at least the plurality of fourth pixels.

20. A medical device, comprising:
  a processor and non-transitory computer readable medium storing instructions that, when executed by the processor, causes the processor to:
    transmit light having a plurality of wavelengths from an illumination source;
    remove at least a subset of a plurality of pixel values detected by a digital image sensor that is communicatively coupled to the processor, wherein the digital image sensor includes a filter array configured to filter the plurality of wavelengths of the light into the plurality of pixel values;
    generate a plurality of estimated pixel values; and
    create a processed image having a partial-resolution frame including the plurality of pixel values and the plurality of estimated pixel values, and omitting at least the subset of the plurality of pixel values from the processed image.

* * * * *